US00PP25623P3

(12) United States Plant Patent
Korlipara

(10) Patent No.: US PP25,623 P3
(45) Date of Patent: Jun. 16, 2015

(54) *DICENTRA* PLANT NAMED 'AMORE ROSE'

(50) Latin Name: ***Dicentra* hybrid**
Varietal Denomination: Amore Rose

(71) Applicant: Terra Nova Nurseries, Inc., Canby, OR (US)

(72) Inventor: Harini Korlipara, Canby, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 174 days.

(21) Appl. No.: 13/986,999

(22) Filed: Jun. 21, 2013

(65) Prior Publication Data

US 2014/0380543 P1 Dec. 25, 2014

(51) Int. Cl.
*A01H 5/02* (2006.01)

(52) U.S. Cl.
USPC ..... Plt./426

(58) Field of Classification Search
USPC ..... Plt./426
See application file for complete search history.

*Primary Examiner* — Susan McCormick Ewoldt

(74) *Attorney, Agent, or Firm* — Klarquist Sparkman, LLP

(57) ABSTRACT

A new and distinct form of *Dicentra* plant characterized by its soft, feathery blue green foliage, a compact habit, medium dark rose flowers on short flower stalks, repeat blooming, and good vigor.

1 Drawing Sheet

Botanical denomination: *Dicentra* hybrid.
Variety designation: 'Amore Rose'.

BACKGROUND OF THE INVENTION

The present invention relates to a new and distinct cultivar of *Dicentra*, of the family Fumariaceae, known by the cultivar name, 'Amore Rose'. This plant originated from planned cross between. The seed parent is *Dicentra* 'Burning Hearts', U.S. Plant Pat. No. 20,797, and the pollen parent was a proprietary unreleased *Dicentra* hybrid seedling (*Dicentra peregrina*×(*D. formosa subsp. oreganaxD. eximia*)). This seedling selection stood out with its unique characteristics.

This new cultivar is uniquely characterized by:

1. soft, feathery blue green foliage,
2. a compact habit,
3. medium large deep rose flowers on short flower stalks,
4. repeat blooming over a long season, and
5. good vigor.

Compared to the seed parent, *Dicentra* 'Burning Hearts', U.S. Plant Pat. No. 20,797, the new cultivar a bigger habit, and bigger leaves that are less silver. The new cultivar is a more vigorous plant and longer blooming.

Compared to the pollen parent the new cultivar has blue green foliage color rather than green and a tighter habit.

Compared to co-pending application for *Dicentra* 'Amore Pink' (U.S. Ser. No. 13/986,956), the new cultivar has deep rose flowers rather than silver pink.

The new variety has been reproduced only by asexual propagation. Each of the progeny exhibits identical characteristics to the original plant. Asexual propagation by micropropagation as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWINGS

FIG. 1 shows a mass planting of *Dicentra* 'Amore Rose' in the garden in early June in Canby, Oreg.

FIG. 2 shows a plant in the garden in May in Canby, Oreg.

DETAILED PLANT DESCRIPTION

The following is a detailed description of the new *Dicentra* cultivar based on observations of 6-month-old specimens grown in a cool greenhouse in gallon containers then moved outside in the shade to bloom in June in Canby, Oreg. Canby is Zone 8 on the USDA Hardiness map. Temperatures range from a high of 95° F. in August to 32° F. in January. Normal rainfall in Canby is 42.8 inches per year. The color descriptions are all based on *The Royal Horticultural Society Colour Chart,* $5^{th}$ edition.

Plant:

*Type*.—Herbaceous perennial.
*Form*.—Clumping rosette.
*# crowns*.—1.
*Cold hardiness*.—USDA Zone 5.
*Size*.—Foliage grows to 13 cm tall to top of foliage and 41 cm wide.
*Vigor*.—Excellent.

Leaf:

*Type*.—Ternately compound.
*Arrangement*.—Rosette.
*Shape*.—Broadly ovate to triangular in outline, leaflets usually ovate in outline.
*Lobing/division*.—20 to 44 leaflets per leaf, leaflets lobed and tip acute.
*Venation*.—Pinnate.
*Blade size*.—Grows to 16 cm long and 15.5 cm wide.
*Surface texture*.—Glabrous.
*Petiole description*.—Grows to 13 cm long and 3.5 mm wide, base clasping, Grey Brown N199A.

*Leaf color*.—Newly opening leaves (including veins) top side Yellow Green 147B, bottom side closest to 147B with veins and margins tinted Greyed Purple 187A, margins curl up to show color on top; older leaves (including veins) topside Green 136B, bottom side N138B.

Inflorescence:

*Type*.—Scapose panicle.

*Number of flowers*.—About 19 to 27 per panicle, increasing with older plants.

*Number of panicles in first spring flush*.—1 to 7.

*Peduncle description*.—Grows to 17 cm long and 2.5 mm wide, glabrous, Brown 200B.

*Pedicel description*.—20 mm long, 1 mm wide, Brown 200B.

*Bloom period*.—April to July in Canby, Oreg.

Flower bud:

*Size*.—20 mm long and 10 mm wide at the widest point prior to opening.

*Description*.—Oblong with the base wider than the tip and heart-shaped.

*Color*.—Purple 71B with tips Purple N79A.

Flower:

*Type*.—Zygomorphic.

*Corolla description*.—Pendulous, heart-shaped on bottom half, laterally compressed, 4 petals in 2 opposed pairs; outer petal pair pouched at the base forming the heart shape, reflexed on top ⅓ and cupped at tip, 20 mm long and spreading 16 mm wide on top, margins entire, tip acute, glabrous inside and out; outside color Red Purple 64A with tips Purple N79B, inside color Purple 75A on bottom ¾ and Purple N79B edged White N155B on top ¼ where cupped; inner petal pair tongue shaped and connected at the tip and bottom 10 mm, 21 mm long and to 7 mm wide, with convex inner face and crested apex; margins entire, tip apiculate; both sides with crest Purple N79B and face White N155B.

*Calyx description*.—2 sepals, 5 mm long and 3 mm wide, elliptic, tip acute, margin entire, both sides glabrous and Purple N79A.

*Pistil description*.—One, 12 mm long, ovary 6 mm long and 2.5 mm wide, Green N137A; style 9 mm long, Yellow Green 145C, stigma is arrow-shaped, 0.5 mm wide, Greyed Purple 187A.

*Stamen description*.—2 in number, compound with 3 partially fused sections in each inner petal, 15 mm long, filaments 13 mm long and to 2 mm wide, White NN155C, anthers 2 in six sections, 1.5 mm long, ovoid, Green Yellow 1D, pollen Yellow 11D.

*Fragrance*.—Slight, sweet.

*Lastingness*.—A panicle blooms for about 4 weeks on the plant.

Fruit and seed: No fruit or seed has been observed to date.

Pest and disease tolerance: The new cultivar is typical to the genus. No known resistances to pests or diseases. No problems have been found in Canby, Oreg.

I claim:

1. A new and distinct form of *Dicentra* plant as hereby illustrated and described.

* * * * *

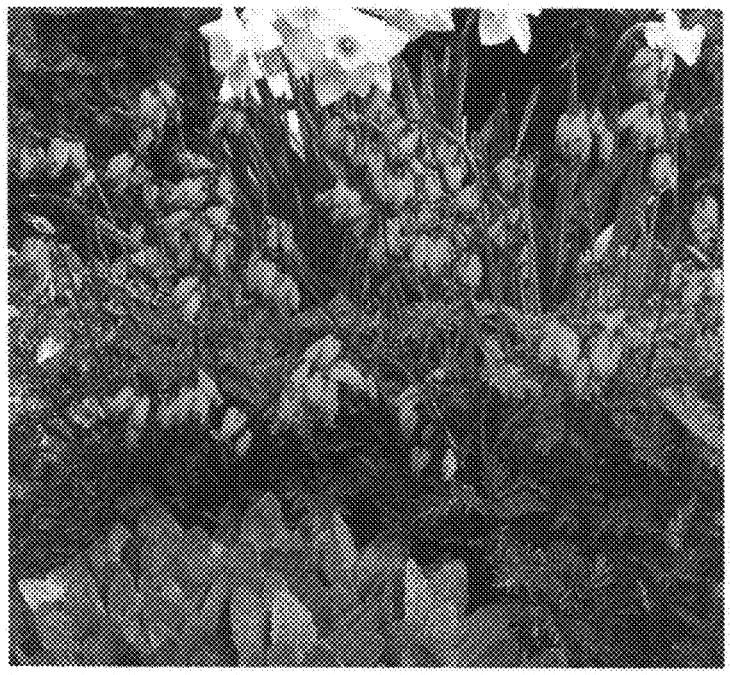

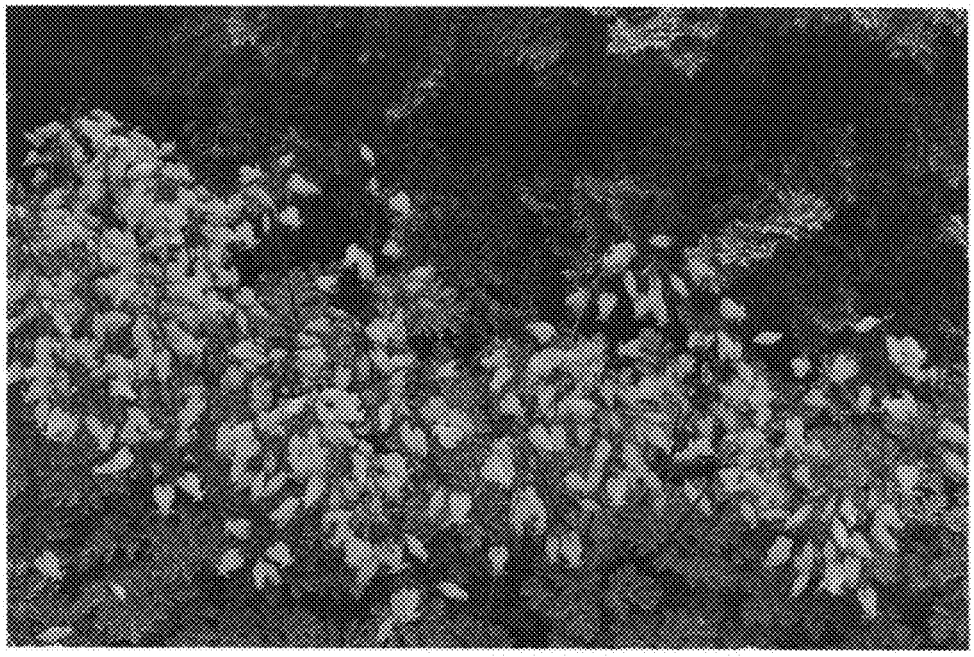
FIG. 1 above, FIG. 2 below